US 9,332,890 B2

(12) United States Patent
Ozawa (10) Patent No.: US 9,332,890 B2
(45) Date of Patent: *May 10, 2016

(54) PROCESSOR FOR ELECTRONIC ENDOSCOPE AND ELECTRONIC ENDOSCOPE APPARATUS

(75) Inventor: Ryo Ozawa, Saitama (JP)

(73) Assignee: HOYA CORPORATION, Tokyo (JP)

( * ) Notice: Subject to any disclaimer, the term of this patent is extended or adjusted under 35 U.S.C. 154(b) by 327 days.

This patent is subject to a terminal disclaimer.

(21) Appl. No.: 13/813,231

(22) PCT Filed: Aug. 25, 2011

(86) PCT No.: PCT/JP2011/069134
§ 371 (c)(1),
(2), (4) Date: Jan. 30, 2013

(87) PCT Pub. No.: WO2012/046518
PCT Pub. Date: Apr. 12, 2012

(65) Prior Publication Data
US 2013/0123576 A1    May 16, 2013

(30) Foreign Application Priority Data

Oct. 6, 2010 (JP) ................................. 2010-226806

(51) Int. Cl.
*A61B 1/00* (2006.01)
*A61B 1/04* (2006.01)
(Continued)

(52) U.S. Cl.
CPC ........... *A61B 1/00009* (2013.01); *A61B 1/0002* (2013.01); *A61B 1/0005* (2013.01);
(Continued)

(58) Field of Classification Search
CPC .......................................................... A61B 1/05

USPC ........................................................... 348/65
See application file for complete search history.

(56) References Cited

U.S. PATENT DOCUMENTS 4,901,143 A    2/1990    Uehara et al.
5,270,810 A    12/1993   Nishimura
(Continued)

FOREIGN PATENT DOCUMENTS

CN    101005795    7/2007
CN    101040774    9/2007
(Continued)

OTHER PUBLICATIONS

Japan Office action in Japan Patent Application No. 2010-226806, dated Jun. 2, 2014 along with an english translation thereof.
(Continued)

*Primary Examiner* — Dave Czekaj
*Assistant Examiner* — Alison Slater
(74) *Attorney, Agent, or Firm* — Greenblum & Bernstein, P.L.C.

(57) ABSTRACT

A processor for an electronic endoscope includes first and second image storing units and a controller, which in a first mode, image data is converted sequentially into a video signal and is outputted while being stored sequentially in the first and second image storing units. In a second mode, image data stored in the first image storing unit is outputted while generated image data is sequentially stored in the second image storing unit. In a third mode, image data stored in the second image storing unit is outputted while generated image data is sequentially stored in the first image storing unit. In the second and third modes, it is possible to switch between a first playback mode that continuously outputs the multiple stored image data and a second playback mode that repeatedly outputs one of the multiple stored image data.

10 Claims, 6 Drawing Sheets

(51) Int. Cl.
 *H04N 5/225* (2006.01)
 *H04N 7/18* (2006.01)
 *H04N 1/46* (2006.01)
 *G02B 23/24* (2006.01)
 *A61B 1/045* (2006.01)
 *A61B 1/05* (2006.01)
 *A61B 5/00* (2006.01)
 *H04N 5/232* (2006.01)

(52) U.S. Cl.
 CPC ............ *A61B1/00006* (2013.01); *A61B 1/042* (2013.01); *A61B 1/045* (2013.01); *A61B 1/05* (2013.01); *A61B 5/0031* (2013.01); *G02B 23/2476* (2013.01); *H04N 5/23232* (2013.01); *H04N 7/183* (2013.01); *H04N 2005/2255* (2013.01)

(56) References Cited

U.S. PATENT DOCUMENTS

| | | | |
|---|---|---|---|
| RE34,504 | E | 1/1994 | Uehara et al. |
| 5,617,136 | A | 4/1997 | Iso et al. |
| 6,489,987 | B1 | 12/2002 | Higuchi et al. |
| 2007/0223797 | A1 | 9/2007 | Kaneko |
| 2008/0303898 | A1* | 12/2008 | Nishimura ..................... 348/65 |
| 2009/0040235 | A1 | 2/2009 | Matsuda |
| 2009/0135249 | A1 | 5/2009 | Hirakawa |
| 2011/0122068 | A1* | 5/2011 | Venon ........................ 345/169 |
| 2013/0123576 | A1 | 5/2013 | Ozawa |

FOREIGN PATENT DOCUMENTS

| | | | |
|---|---|---|---|
| CN | 101778591 | 7/2010 | |
| JP | 63-214231 | 9/1988 | |
| JP | 1-279689 | 11/1989 | |
| JP | 4-33651 | 2/1992 | |
| JP | 4-71546 | 3/1992 | |
| JP | 7-289507 | 11/1995 | |
| JP | 10-323326 | 12/1998 | |
| JP | 11-197104 | 7/1999 | |
| JP | 11-216107 | 8/1999 | |
| JP | 2002-65667 | 3/2002 | |
| JP | 3497231 | 2/2004 | |
| JP | 2007-301398 | 11/2007 | |
| JP | 2008-302146 | 12/2008 | |
| WO | WO 2007077554 A2 * | 7/2007 | ............... H04N 1/46 |
| WO | WO 2010086751 A2 * | 8/2010 | ................ G06T 5/00 |

OTHER PUBLICATIONS

U.S. Appl. No. 13/823,996 to Ryo Ozawa, filed Mar. 15, 2013.
China Office action, dated Nov. 17, 2014 along with an English translation thereof.
China Office action in China Patent Application No. 201180051851.3, dated Dec. 3, 2014 along with an English translation thereof.
Office Action issued in U.S. Appl. No. 13/823,996, dated Jun. 18, 2015.

* cited by examiner

PROCESSOR FOR ELECTRONIC ENDOSCOPE AND ELECTRONIC ENDOSCOPE APPARATUS

TECHNICAL FIELD

The present invention relates a processor for an electronic endoscope which processes an image signal from an electronic endoscope and displays video, for example, on a monitor, and an electronic endoscope apparatus including the above described electronic endoscope and the processor.

BACKGROUND ART

Electronic endoscope apparatuses have been widely used for observation and diagnosis for a body cavity. The electronic endoscope apparatus includes an image pick-up device at its tip portion, and includes an electronic endoscope which outputs an image signal of an image shot by the image pick-up device, and a processor for the electronic endoscope which processes the image signal from the electronic endoscope, converts the image signal into a video signal having a predetermined format (e.g., a video signal in NTSC format) and displays the video, for example, on a monitor.

Generally, the processor for the electronic endo scope displays the image picked up by the electronic endoscope on the monitor as a moving image. Further, the processor for the electronic endo scope has the function of displaying the picked up image as a still image in order to make it possible to more specifically observe an observation target portion.

Displaying of the still image is triggered, for example, upon detection of pressing of an operation button provided on the electronic endoscope or the processor for the electronic endoscope. That is, a frame displayed on a monitor when the operation button is pressed or a next frame is continued to be displayed as a still image.

In the above described configuration, a user of the electronic endoscope is required to press the operation button at an appropriate timing while checking the moving image displayed on the monitor. However, since it is necessary to operate the electronic endoscope and press the operation button while checking the monitor, it is not easy to obtain a desired still image due to delay of the pressing timing of the operation button. For example, when the operation button is pressed while the observation target portion is moving, a problem arises that a blurry still image or a still image affected by color drift is obtained.

In order to prevent occurrence of a blurry image or a still image affected by color drift, a processor for an electronic endoscope having the function described in Japanese Patent Publication No. JP3497231B (hereafter, referred to as patent document 1) has been proposed. The processor for the electronic endoscope described in patent document 1 is configured to store image data of a plurality of latest frames in a memory, and when an operation for obtaining a still image (e.g., pressing of an operation button) is performed, the processor selects an image having a lower level of blur or color drift and displayed the selected image as a still image on the monitor.

SUMMARY OF THE INVENTION

Through use of the processor for the electronic endoscope described in patent document 1, a still image having a lower level of blur or color drift can be obtained. However, in the configuration of the patent document 1, the obtained still image having a lower level of blur or color drift does not always correspond to a desired still image, and therefore there is a case where re-obtaining of a still image is needed. In addition, in the configuration of patent document 1, no image data is stored in the memory during a time period from conducting of operation for obtaining a still image to displaying of the still image on the monitor. Therefore, when obtaining of a still image is required again, it is necessary to wait until image data is stored in the memory again, which causes a problem that a diagnosis time extends.

The present invention is made to solve the above described problem. That is, the objection of the invention is to provide a processor for an electronic endoscope and an electronic endoscope apparatus capable of reliably obtaining a desired still image in a short period of time.

To achieve the above described object, a processor for an electronic endoscope according to the invention includes first and second image storing means and a control means, and the control means executes control in one of: a first mode in which the image data is sequentially converted into the video signal and is outputted, and is sequentially stored in the first and second image data storing means; a second mode in which the image data stored in the first image storing means is outputted, and the generated image data is sequentially stored in the second image storing means; and a third mode in which the image data stored in the second image storing means is outputted, and the generated image data is sequentially stored in the first image storing means. In the second mode and the third mode, a first reproduction mode in which a plurality of image data stored in the first and second image storing means are successively outputted and a second reproduction mode in which one of the plurality of image data stored in the first and second image storing means is repeatedly outputted can be switched.

In the above described configuration, when an image shot by the electronic endo scope is observed as a moving image, control is performed in the first mode, and when a still image is obtained, the mode is switched to the second or third mode, and the immediately previous plurality of image data stored in the first and second image storing means is displayed successively. Then, appropriate image data is selected and displayed on the monitor. In the above described configuration, the image data shot by the electronic endoscope is stored both in the first image storing means and the second image storing means. Therefore, even when a user operates to display a moving image by returning to the first mode after a still image is displayed in the second mode and to try to immediately obtain another still image while checking the moving image, the user can obtain a still image in the third mode because the immediately previous image data including the image shot by the electronic endoscope in the second mode is stored in the second image storing means.

When the control means may switch from the first reproduction mode to the second reproduction mode, the image data outputted immediately before switching to the second reproduction mode is repeatedly converted into the video signal and is outputted.

In the first reproduction mode, the plurality of image data stored in each of the first and second image storing means may be sequentially converted into the video signal in reverse chronological order in regard to a stored time and may be outputted. In this case, when the mode is switched from the first mode to the second or third mode, a moving image reproduced in a reverse direction from a time point of the switching is displayed on the monitor.

In the first reproduction mode, the plurality of image data stored in each of the first and second image storing means may be sequentially converted into the video signal in chronological order in regard to a stored time and may be outputted. In this case, when the mode is switched from the first mode to the second or third mode, a moving image reproduced in a forward direction from a time point wound back for a certain time period (corresponding to the storage capacity of the first and second image storing means) from the time point of the switching is displayed on the monitor.

In the first reproduction mode, each of the plurality of image data stored in the first and second image storing means may be successively converted into the video signal a plurality of times and may be outputted. In such a configuration, when the first mode is switched to the second or third mode, one frame of image data stored in the first and second image storing means is continuously displayed over a plurality of frames. That is, in this configuration, in the state where a plurality of image data is successively converted into the video signal and is outputted in the second or third mode, a moving image is displayed on the monitor in a slow reproducing manner.

The processor for an electronic endoscope may further comprise a judgment means which receives an input of a control signal for switching from the first mode to the second or the third mode and makes a judgment on which of the second mode and the third mode the control means switches to when the control signal is inputted, and the control means may switch from the first mode to the second or the third mode based on a judgment result of the judgment means.

In this case, the judgment means may make a judgment such that the second mode and the third mode are alternately switched each time the control signal is inputted.

The judgment means may make a judgment to switch from the first mode to the third mode only when the control signal is inputted within a predetermined time from a time when switching from the second mode to the first mode is performed. In this case, the predetermined time may correspond to a number of pieces of image data which can be stored in the first image storing means.

Preferably, an electronic endoscope apparatus according to the invention comprises one of the above described processors for an electronic endoscope, and comprises: a first input means which receives an input for designating switching from the first mode to the second or third mode; a second input means which receives an input for switching from the first reproduction mode to the second reproduction mode in the second or third mode; and a third input means which receives an input for designating switching from the second and third modes to the first mode by inputting through the first to third input means.

With this configuration, it becomes possible to obtain a still image and to release a displaying state for a still image.

The first input means may be identical with the third input means.

The processor for an electronic endoscope may further comprise a fourth input means which receives an input for switching from the second reproduction mode to the first reproduction mode in the second or the third mode.

With this configuration, when a still image displayed on the monitor once but the still image is hard to view due to a large degree of blur and color shift, it is possible to move back to the mode where the image data stored in the first and second image storing means is successively displayed on the monitor, and to obtain a still image again.

Furthermore, in this case, the second input means may be identical with the fourth input means.

As described above, according to the invention, a processor for an electronic endo scope and an electronic endo scope apparatus capable of reliably obtaining a desired still image in a short period of time are realized.

EMBODIMENTS FOR CARRYING OUT THE INVENTION

In the following, embodiments of the present invention are explained in detail with reference to the accompanying drawings.

First Embodiment

Figure 1:
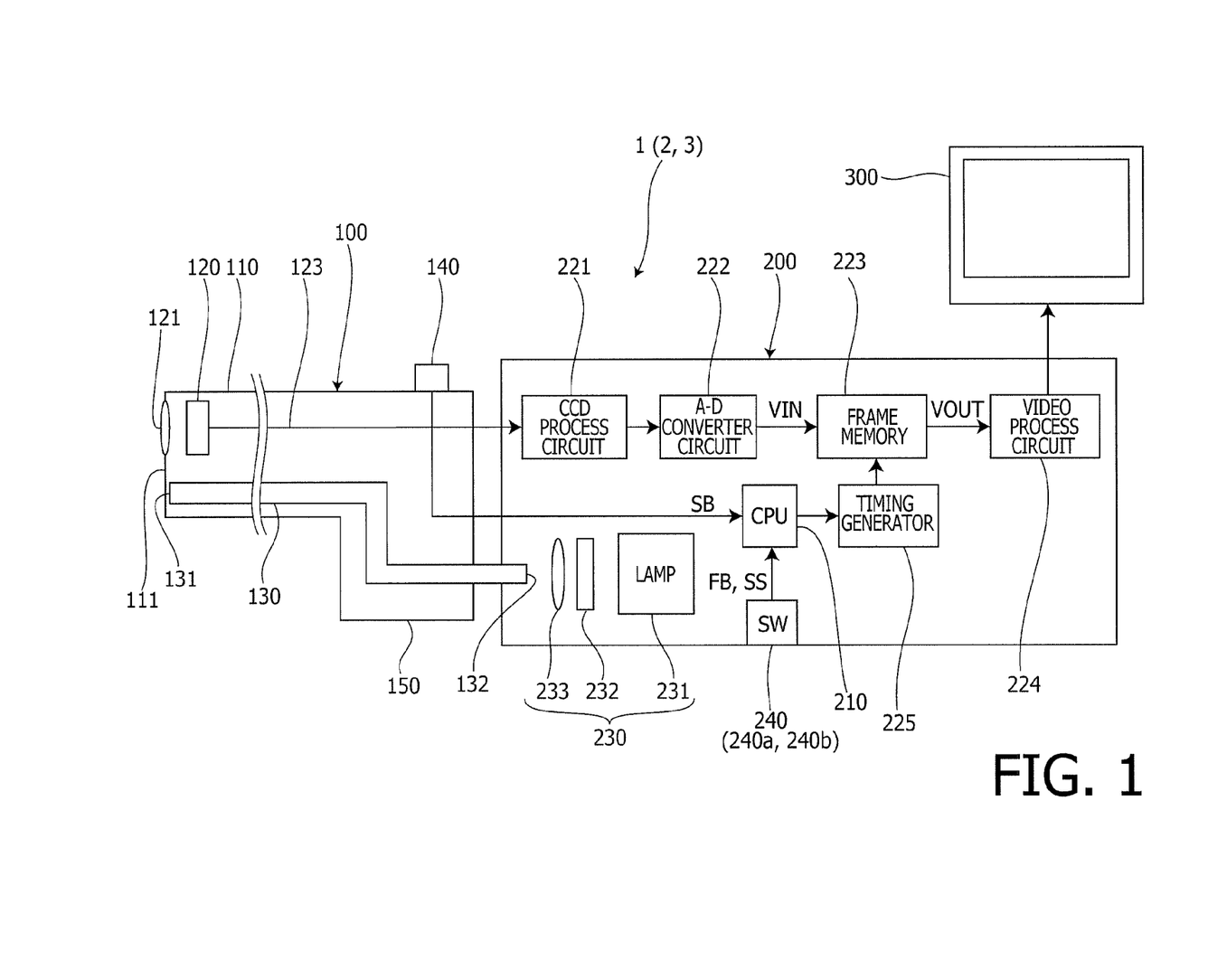
FIG. 1 is a block diagram of an electronic endoscope apparatus according to a first embodiment of the invention.

An electronic endoscope apparatus 1 according to a first embodiment of the invention is explained with reference to FIGS. 1 to 4. FIG. 1 is a block diagram of the electronic endoscope apparatus 1 according to the first embodiment of the invention. The electronic endoscope apparatus 1 according to the embodiment includes an electronic endoscope 100, a processor 200 for the electronic endoscope, and a monitor 300.

An objective lens 121 and an image pick-up device 120 are accommodated in the vicinity of a tip portion (an insertion tube tip part) 111 in an insertion tube 110 of the electronic endoscope 100. The objective lens 121 converges a subject image near to the insertion tube tip part 111 onto a light receiving surface of the image pick-up device 120.

The image pick-up device 120 outputs an image signal corresponding to the image converged onto the light receiving surface. The image signal is transmitted to a CCD process circuit 221 of the processor 200 for the electronic endoscope via a signal cable 123 inserted into the inside of the insertion tube 110. The image pick-up device 120 is controlled by timing pulses inputted to the image pick-up device 120 from a CCD driving circuit (not shown) accommodated in a connector portion 150 of the electronic endo scope 100. Output timing of the timing pulses by the CCD driving circuit is controlled by a microprocessor (not shown) accommodated in the connector portion 150. In FIG. 1, the electronic endoscope 100 and the processor 200 for the electronic endoscope are illustrated apart from each other for convenience of explanation; however, when the electronic endo scope 100 is used, the electronic endo scope 100 is connected to the processor 200 for the electronic endoscope electrically and optically by the connector portion 150.

In the processor 200 for the electronic endoscope, the CCD process circuit 221, an A-D converter circuit 222, a frame memory 223, a video process circuit 224, a timing generator 225, a CPU 210, a switch 240, and an illumination device 230 are accommodated. The CCD process circuit 221 executes processes, such as a noise cut process and an amplifying process, for the image signal inputted from the image pick-up device 120, and transmits the signal to the A-D converter circuit 222. The A-D converter circuit 222 converts the analog image signal received from the CCD process circuit 221 into digital image data, and outputs the image data to the frame memory 223. The frame memory 223 is constituted by a memory capable of storing a plurality of frames of image data (which is described later), and is configured to store the image data under control of the timing generator 225 and to output the stored image data to the video process circuit 224. The video process circuit 224 converts the image data outputted from the frame memory 223 into a video signal (e.g., an NTSC signal) in a predetermined format, and outputs the video signal to the monitor 300 connected to the processor 200 for the electronic endoscope. Through the above described processes, the image near the insertion tube tip part 111 of the electronic endoscope 100 is displayed on the monitor 300.

The CPU 210 of the processor 200 for the electronic endo scope is connected to each component of the processor 200 for the electronic endo scope, such as the switch 240 and the timing generator 255, and totally controls the processor 200 for the electronic endoscope and the electronic endoscope 100 in accordance with programs stored in a memory (not shown). The switch 240 is a user interface through which a user makes settings or inputs instructions to the processor 200 for the electronic endoscope. For example, the switch 240 is a freeze button 240a for obtaining a still image. The CPU 210 makes settings or changes the settings of the processor 200 for the electronic endoscope and the electronic endoscope 100 in accordance with an input from the switch 240. In this embodiment, when the electronic endo scope 100 is connected to the processor 200 for the electronic endoscope, a scope button 140 of the electronic endoscope 100 is connected to the CPU 210, and the CPU 210 is configured to be able to monitor the state of the scope button 140. That is, when the scope button 140 is pressed, a scope button input signal SB indicative of pressing of the scope button 140 is transmitted to the CPU 210, and the CPU 210 is able to judge whether the scope button 140 of the electronic endo scope 100 is pressed.

The processor 200 for the electronic endoscope includes the illumination device 230 which generates illumination light for illuminating the portion near the insertion tube tip part 111 of the electronic endoscope 100. In the following, explanation is given for the function of the processor 200 for the electronic endoscope as an illumination device.

As shown in FIG. 1, the processor 200 for the electronic endoscope includes a lamp 231, a diaphragm 232 and a condenser lens 233. A light guide 130 is provided to extend from the insertion tube 110 to the connector portion 150 of the electronic endoscope 100. A tip 131 of the light guide 130 is arranged near the insertion tube tip part 111 of the electronic endoscope 100, and a light distribution lens (not shown) is arranged near the insertion tube tip part 111.

The lamp 231 accommodated in the processor 200 for the electronic endoscope produces illumination light through supply of power from a lamp power supply circuit (not shown). The produced illumination light is incident on the condenser lens 233 through the diaphragm 232. The light guide 130 is provided to protrude from the connector portion 150, and in the state where the electronic endo scope 100 is connected to the processor 200 for the electronic endo scope, the light guide 130 is inserted into the inside of the processor 200 for the electronic endoscope. In the state where the light guide 130 is inserted into the processor 200 for the electronic endo scope, a proximal end 132 of the light guide 130 is located at a position on which the illumination light collected by the condenser lens 233 is incident. As a result, the illumination light produced by the lamp 231 is incident on the proximal end 132 of the light guide 130, reaches the tip portion 131 through the light guide 130, and illuminates, through the light distribution lens, a living body tissue near the insertion tube tip part 111. The diaphragm 232 is controlled by the CPU 210. That is, by controlling the diaphragm 232, the CPU 210 adjusts the amount of illumination light incident on the proximal end 132 of the light guide 130 from the lamp 231, and alters the intensity of the illumination light.

Figure 2:
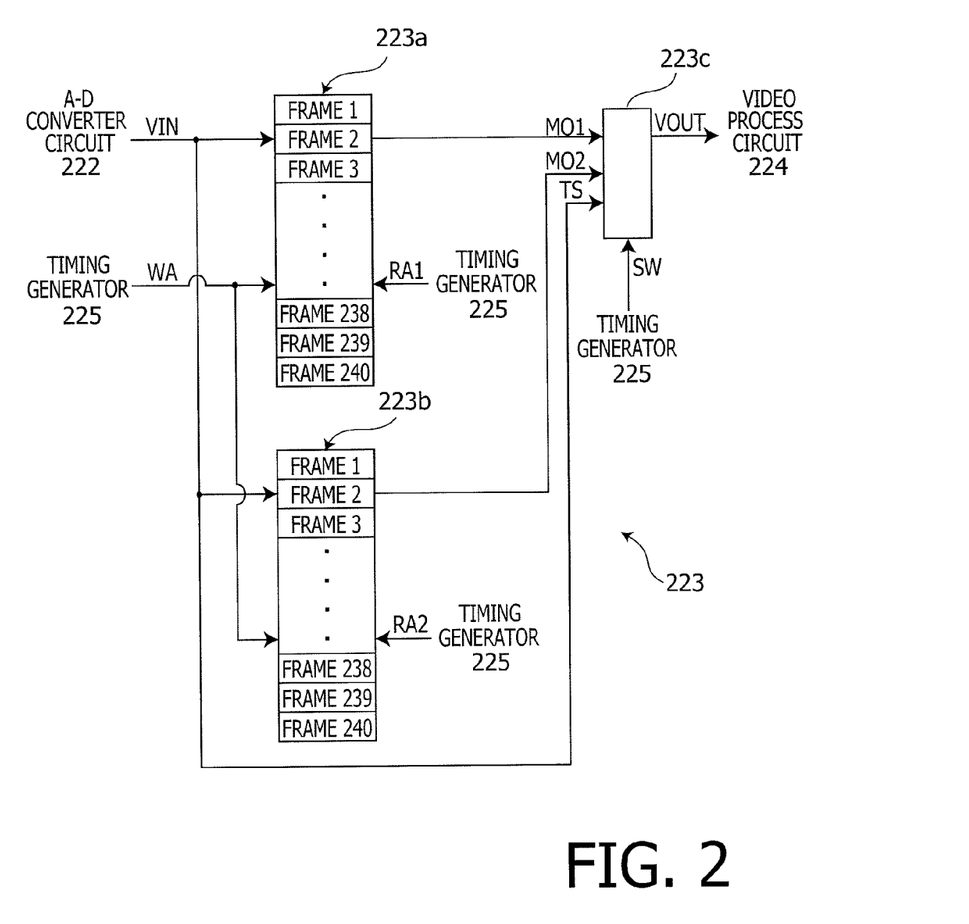
FIG. 2 is a block diagram illustrating a configuration of a frame memory accommodated in a processor for an electronic endoscope according to the first embodiment of the invention.

FIG. 2 is a block diagram illustrating a configuration of the frame memory 223 accommodated in the processor 200 of the electronic endoscope according to the embodiment.

As shown in FIG. 2, the frame memory 223 includes a first memory 223a, a second memory 223b and a switch circuit 223c. Each of the first memory 223a and the second memory 223b is constituted, for example, by a ring-type memory including a DRAM, and the digital image data outputted from the A-D converter circuit 222 is inputted as input image data VIN. Each of the first memory 223a and the second memory 223b according to the embodiment is configured to be able to store 240 frames of image data. Each of the first memory 223a and the second memory 223b is connected to the timing generator 225, and a writing address WA and a first memory read address RA1 are inputted to the first memory 223a, and the writing address WA and a second memory read address RA2 are inputted to the second memory 223b.

The writing address WA is data representative of an address on the first memory 223a and the second memory 223b storing the input image data VIN, and in this embodiment, the writing address WA is inputted in common to the first memory 223a and the second memory 223b. Each of the first memory 223a and the second memory 223b stores the input image data VIN at an address indicated by the writing address WA when being set as a writable state (i.e., in a read-inhibited state) by the timing generator 225. The input image data VIN stored in the first memory 223a and the second memory 223b can be read by designating the first memory read address RA1 and the second memory read address RA2. When the first memory 223a and the second memory 223b are not set as the read-inhibited state (the writable state) by the timing generator 225, the image data stored at the first memory read address RA1 and the second memory read address RA2 are respectively read from the first memory 223a and the second memory 223b, and the image data is outputted as a first memory output MO1 and a second memory output MO2.

The switch circuit 223c is a circuit for performing switching of the input signals, and is constituted, for example, with a multiplexer. To the switch circuit 223c, the first memory output MO1, the second memory output MO2 and a through image signal TS (i.e., the input image data VIN) are inputted, and under control of the timing generator 225, one of the first memory output MO1, the second memory output MO2 and the through image signal TS is selected and is outputted as an output image data VOUT. Then, the output image data VOUT outputted from the switch circuit 223c is transmitted to the video process circuit 224.

As described above, the frame memory 223 accommodated in the processor 200 for the electronic endoscope according to the embodiment includes the first memory 223a and the second memory 223b each of which stores the plurality of frames of image data, and the image data stored in these memories is read under control of the timing generator 225. The timing generator 225 is controlled by the CPU 210 (FIG. 1), and by execution of a program stored in a memory (not shown) by the CPU 210, an image recording/reproducing operation which is described later is executed.

Figure 3:
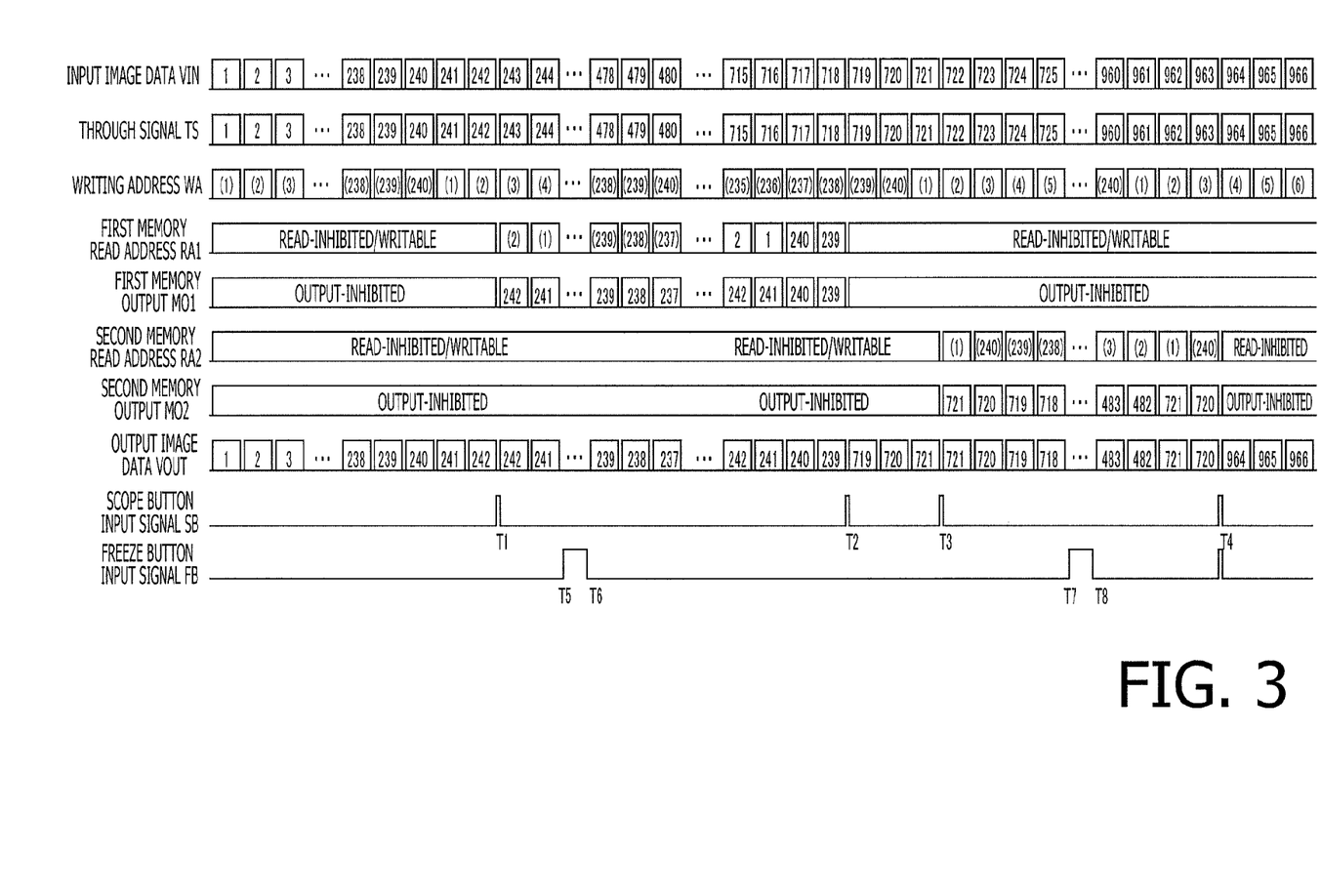
FIG. 3 is a timing chart illustrating an image record/reproduction operation executed in the electronic endoscope apparatus according to the first embodiment of the invention.

Next, the image recording/reproducing operation executed by the electronic endoscope apparatus 1 according to the embodiment is explained with reference to FIG. 3. FIG. 3 is a timing chart illustrating the image recording/reproducing operation executed by the electronic endoscope apparatus 1 according to the embodiment. In FIG. 3, to signals common to FIGS. 1 and 2, the same reference numbers are assigned.

When the electronic endoscope 100, the processor 200 for the electronic endoscope and the monitor 300 are turned on, as described above, the image signal outputted from the image pick-up device 120 is transmitted to the CCD process circuit 221, and is digitized by the A-D conversion circuit 222, and then the input image data VIN is sequentially inputted to the frame memory 223. The CPU 210 of the processor 200 for the electronic endoscope executes the program stored in the memory (not shown) to start the image recording/reproducing operation.

FIG. 3 shows the states of each signal (data) inputted to or outputted from the frame memory 223, the scope button input signal SB indicative of pressing of the scope button 140 and the freeze button input signal FB indicative of pressing of the freeze button 240a. Numbers (without parentheses) assigned to the input image data VIN is used for convenience of explanation, and indicates the frame number of the input image data VIN sequentially inputted to the frame memory 223. In addition, numbers (without parentheses) assigned to the through signal TS, the first memory output MO1, the second memory output MO2 and the output image data VOUT indicate the relationship between these signals and the input image data VIN. For example, output "238" of the output image data VOUT indicates that the input image data VIN inputted to the frame memory 223 as "frame number: 238" is outputted. Furthermore, numbers with parentheses assigned to the writing address WA, the first memory read address RA1 and the second memory read address RA2 indicate the addresses to be accessed in the first memory 223a and the second memory 223b.

As shown in FIG. 3, in the state where the first memory 223a and the second memory 223b are in the writable state (the read-inhibited state) (i.e., during a time period to the time T1 at which the scope button input signal SB is inputted), when the input image data VIN is inputted to the frame memory 223, the input image data VIN is stored at the address indicated by the writing address WA in the first memory 223a and the second memory 223b. The writing address WA is incremented each time the input image data VIN is stored under control of the timing generator 225. Therefore, in this state, the input image data VIN successively inputted to the frame memory 223 is stored in the first memory 223a and the second memory 223b at the address indicated by the writing address WA. As described above, since each of the first memory 223a and the second memory 223b is constituted by the ring-type memory capable of storing 240 frames of image data, after the image data of the 240-th frame is stored, the writing address WA is set as "1", and the memory area in which the image data of the first frame is stored is overwritten with the image data of the 241-th frame. As described above, during a time period to the time when the scope button 140 is pressed (a time period to the time T1 when the scope button input signal SB is inputted), 240 frames of the image data are sequentially stored in the first memory 223a and the second memory 223b in an updating manner. The switch circuit 223c is configured to select and output the through signal TS until the scope button 140 is pressed, under control of the timing generator 225. Therefore, the same data as the input image data VIN is outputted as the output image data VOUT. As described above, the state where the input image data VIN is sequentially stored in the first memory 223a and the second memory 223b and the through signal TS is outputted as the output image data VOUT is referred to as a first mode.

In the first mode, when the CPU 210 detects that the scope button 140 is pressed (T1), the CPU 210 controls the timing generator 225 to execute a first rewind reproduction process. When the first rewind reproduction process is executed, the timing generator 225 sets the first memory 223a in a writing-inhibited state (a readable state) under control of the CPU 210, and after switching the output of the switch circuit 223c to the first memory output MO1, the timing generator 225 sets the first memory read address RA1 to the immediately previous value of the wiring address WA. Then, each time the new input image data VIN is inputted to the frame memory 223, the first memory read address RA1 is decremented. In the case of FIG. 3, when the scope button 140 is pressed (T1), the immediately previous wiring address WA is "2", and the data stored at the address is the input image data VIN of the "frame number: 242". Therefore, when the scope button 140 is pressed, initially, "2" is set at the first memory read address RA1, and the input image data VIN of the "frame number: 242" is read out. Then, each time the new input image data VIN is inputted to the frame memory 223, the first memory read address RA1 is decremented as "1", "240", "239" . . . , and the input image data VIN of the frames "frame number: 241", "frame number: 240", "frame number: 239" . . . are sequentially outputted.

As described above, when the first rewind reproduction process is executed, the image data stored in the first memory 223a is read out in reverse chronological order from the latest frame, and as a result the video is outputted in a rewinding manner. The first frame memory 223a according to the embodiment is constituted by a ring-type memory capable of storing 240 frames of image data. Therefore, after the 240 frames are rewound, the video returns again to the latest frame (the frame number 242 in FIG. 3), and the old frames are sequentially read out again. Even when the first rewind reproduction process is executed, the second memory 223b is still in the read-inhibited state (the writable state), and the input image data VIN is sequentially stored at the address indicated by the writing address WA. As described above, the state where the image data is read out from the first memory 223a while storing the input image data VIN in the second memory 223b, and the first memory output MO1 is outputted as the output image data VOUT is referred to as a second mode.

In the second mode, when the CPU 210 detects that the scope button 140 is pressed (T2), the CPU 210 controls the timing generator 225 to stop the first rewind reproduction process. When the first rewind reproduction process is stopped, the timing generator 225 sets the first memory 223a as the read-inhibited state (the writable state), and switches the output of the switch circuit 223c to the through signal TS, under control of the CPU 210. As a result, the input image data VIN is sequentially stored in the first memory 223a again, and the same data as the input image data VIN is outputted as the output image data VOUT. That is, the mode returns to the first mode.

When the CPU 210 detects that the scope button 140 is pressed (T3), the CPU 210 controls the timing generator 225 to execute a second rewind reproduction process. When the second rewind reproduction process is executed, the timing generator 225 sets the second memory 223b as the writing-inhibited state (the readable state), and switches the output of the switch circuit 223c to the second memory output MO2 and sets the second memory read address RA2 to the immediately previous value of the writing address WA, under control of the CPU 210. Then, each time the new input image data VIN is inputted to the frame memory 223, the second memory read address RA2 is decremented. In the case of FIG. 3, when the scope button 140 is pressed (T3), the immediately previous writing address WA is "1", and the data stored at the address is the input image data VIN of the "frame number: 721". Therefore, when the scope button 140 is pressed, initially "1" is set to the second memory read address RA2, and the input image data VIN of the "frame number: 721" is read out. Then, each time the new input image data VIN is inputted to the frame memory 223, the second memory read address RA2 is decremented as "240", "239", "238" . . . , and the input image data VIN of the "frame number: 720", "frame number: 719", "frame number: 718" . . . is sequentially read out and outputted.

As described above, when the second rewind reproduction process is executed, the image data stored in the second memory 223b is sequentially outputted in reverse chronological order from the latest frame, and the video is outputted in a rewinding manner. The second memory 223b according to the embodiment is constituted by a ring-type memory capable of storing 240 frames of image data. Therefore, after the 240 frames are rewound, the video returns again to the latest frame (the frame number 721 in FIG. 3), and the old frames are sequentially read out again. Even when the second rewind reproduction process is executed, the first memory 223a is still in the read-inhibited state (the writable state), and the input image data VIN is sequentially stored at the address indicated by the writing address WA. As described above, the state where the image data is read out from the second memory 223b while storing the input image data VIN in the first memory 223a, and the second memory output MO2 is outputted as the output image data VOUT is referred to as a third mode.

In the third mode, when the CPU 210 detects that the scope button 140 is pressed (T4), the CPU 210 controls the timing generator 225 to stop the second rewind reproduction process. When the second rewind reproduction process is stopped, the timing generator 225 sets the second memory 223b as the read-inhibited state (the writable state), and switches the output of the switch circuit 223c to the through signal TS, under control of the CPU 210. As a result, the input image data VIN is sequentially stored in the second memory 223b again, and the same data as the input image data VIN is outputted as the output image data VOUT. That is, the mode returns to the first mode. It should be noted that, when pressing of the scope button 140 is detected thereafter, the above described mode transition is caused, i.e., each time pressing of the scope button 140 is detected, the mode changes in order of the second mode, the first mode, the third mode, the first mode.

As described above, in the electronic endoscope apparatus 1 according to the embodiment, each time pressing of the scope button 140 is detected by the CPU 210, the mode changes in order of the first mode, the second mode, the first mode, the third mode and the first mode. In the second mode, the image data is read from the first memory 223a while storing the input image data VIN in the second memory 223b, and the first memory output MO1 is outputted as the output image data VOUT. In the third mode, the image data is read out from the second memory 223b while storing the input image data VIN in the first memory 223a, and the second memory output MO2 is outputted as the output image data VOUT. That is, even when one of the first memory 223a and the second memory 223b is set as the readable state (i.e., the writing-inhibited state), the other continues to sequentially store the input image data VIN. Therefore, even when the first rewind reproduction process or the second rewind reproduction process is running, the latest 240 frames of image data can be stored in one of the first memory 223a and the second memory 223b. Therefore, as described later, in this embodiment, a still image is obtained in the second mode or the third mode so as to make it possible to repeatedly re-shoot a still image without the need for waiting for storing of the image data in a memory.

Figure 4:
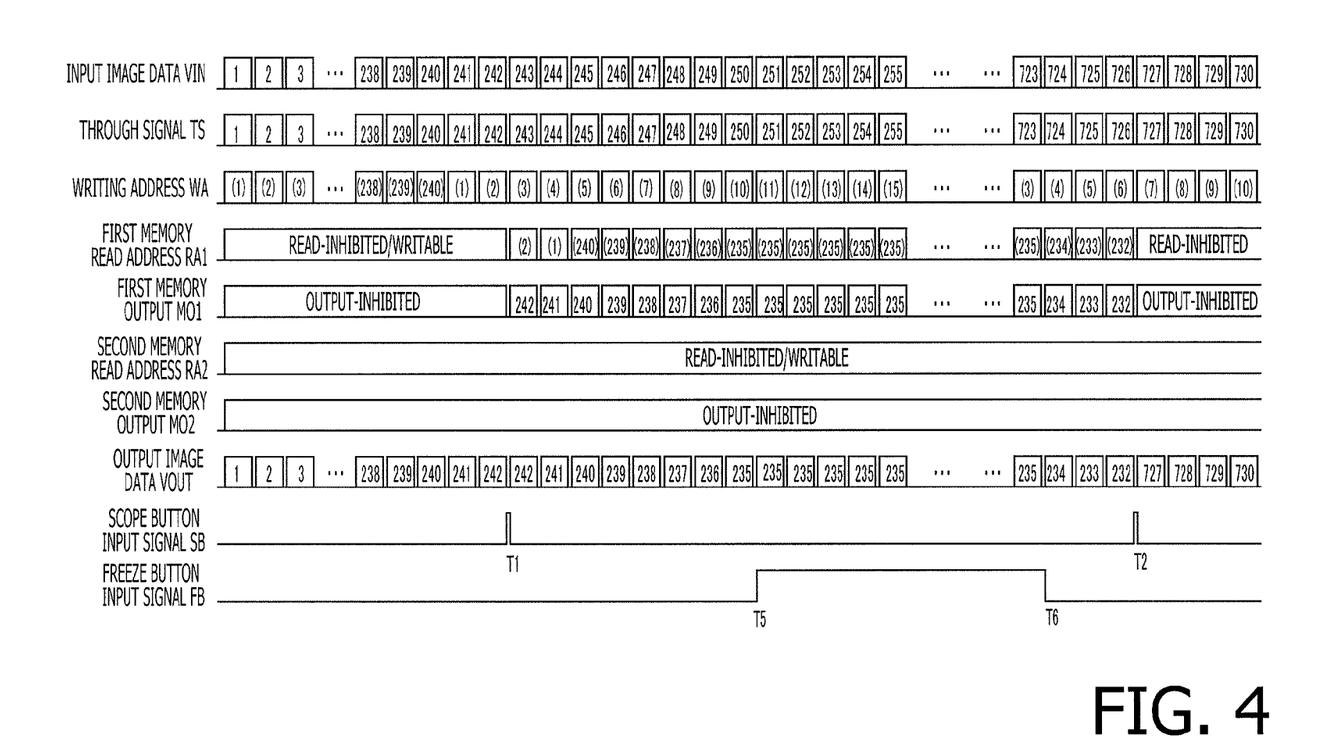
FIG. 4 is a timing chart illustrating a still image reproduction operation executed by the electronic endoscope apparatus according to the first embodiment of the invention.

FIG. 4 is a timing chart illustrating a still image reproduction operation executed by the electronic endoscope apparatus 1 according to the embodiment, and illustrates in detail the timing corresponding to T5 to T6 of FIG. 3. In FIG. 4, to signals which are common to FIG. 3, the same reference numbers are assigned.

In the second mode, when the CPU 210 detects that the freeze button 240a (FIG. 1) is pressed (T5), the CPU 210 controls the timing generator 255 to stop decrement of the first memory address RA1, and the first rewind reproduction process is stopped temporarily. Then, while the freeze button 240a (FIG. 1) is pressed (the time period of T5 to T6), the first memory read address RA1 is maintained at the value immediately before pressing of the freeze button 240a by the CPU 210 ("235" in the case of FIG. 4). Therefore, while the freeze button 240a is pressed, the first memory 223a continues to repeatedly output the input image data VIN of the "frame number: 235" stored in the address. Therefore, while the freeze button 240a is pressed (the time period of T5 to T6), a still image of the "frame number: 235" is displayed on the monitor 300.

The time period of T7 to T8 in FIG. 3 corresponds to the case where the freeze button 240a (FIG. 1) is pressed in the third mode, and in this case a still image can also be obtained as in the case of the time period of T5 to T6.

As described above, in this embodiment, a still image is obtained in the second mode or the third mode. Therefore, it is possible to re-shoot a still image repeatedly without the need for waiting for storing of the image data into a memory. Therefore, when a desired still image cannot be obtained by one operation, a desired still image can be obtained in a relatively short period of time even when re-shooting of a still image is repeatedly performed.

(Variation of First Embodiment)

In the first embodiment, each time pressing of the scope button 140 is detected by the CPU 210, the mode is changed in order of the first mode, the second mode, the first mode, the third mode, the first mode. However, the present invention is not limited to such a configuration. For example, in the case where the mode is changed from the second mode to the first mode, the mode may be changed to the third mode when pressing of the scope button 140 is detected within a predetermined time period from the transition, and the mode may be changed to the second mode again when pressing of the scope button 140 is detected after the predetermined time has elapsed from the transition. Each of the first memory 223a and the second memory 223b according to the first embodiment is configured to be able to store 240 frames of image data. Therefore, when the frame rate of the image signal outputted from the image pick-up device 120 is 60 frames/sec, the image data corresponding to immediately previous 4 seconds is stored in the first memory 223a and the second memory 223b, respectively. In other words, the image data in the first memory 223a and the second memory 223b is completely replaced (refreshed) at every four seconds. Therefore, when the mode is changed from the second mode to the first mode, the mode may move again to the second mode after the time period (four seconds) required for refresh of the first memory 223a has elapsed after the transition.

Second Embodiment

Next, an electronic endoscope apparatus 2 according to a second embodiment of the invention is explained with reference to FIG. 5. The electronic endoscope apparatus 2 according to the second embodiment of the invention has the same configuration as the electronic endoscope apparatus 1 according to the first embodiment shown in FIGS. 1 and 2, and is different from the first embodiment only in regard to the image recording/reproducing operation. In the following, the different point from the first embodiment is explained in detail.

Figure 5:
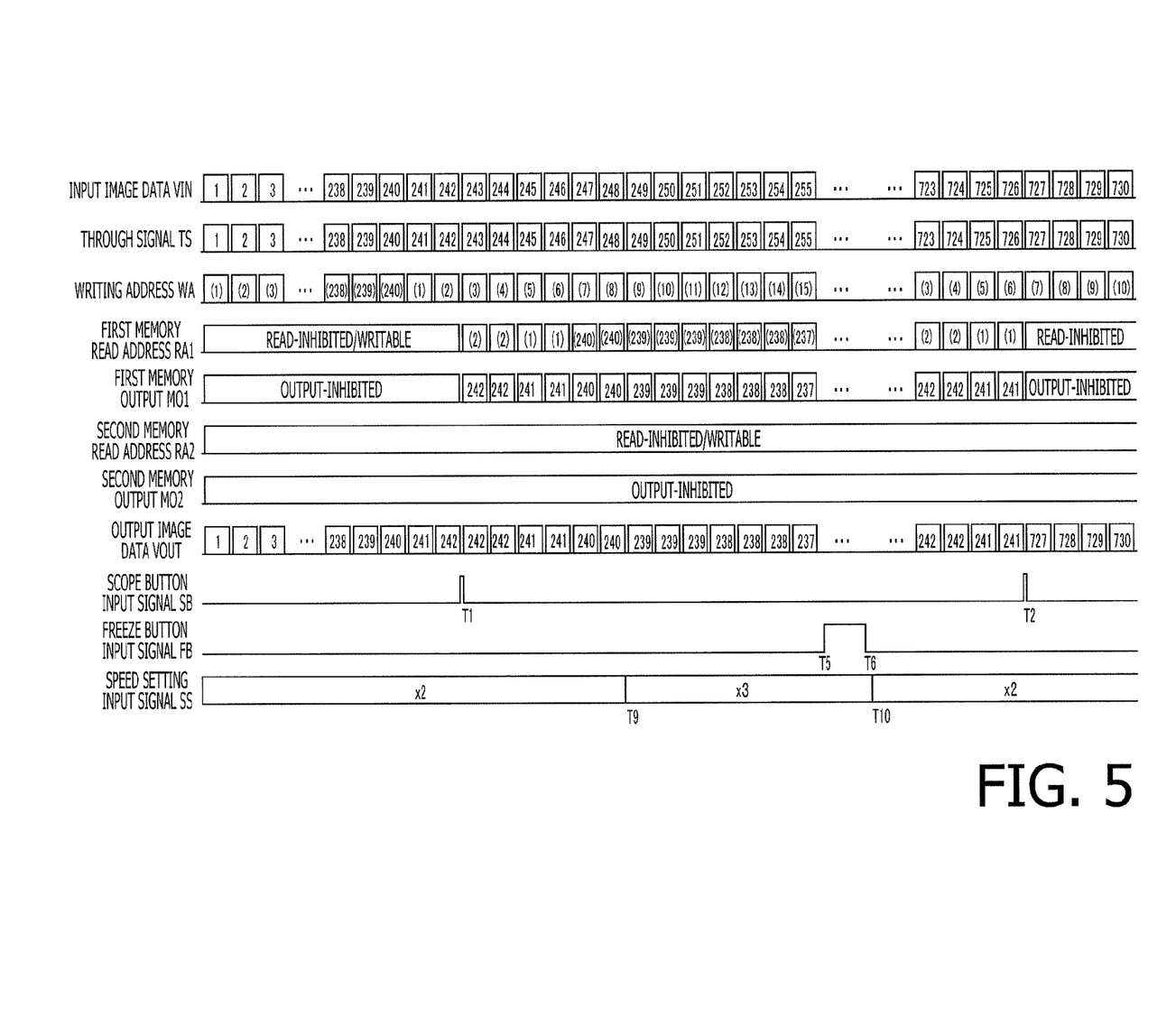
FIG. 5 is a timing chart illustrating an image record/reproduction operation executed in an electronic endoscope apparatus according to a second embodiment of the invention.

FIG. 5 is a timing chart illustrating the image recording/reproducing operation executed by the electronic endoscope apparatus 2 according to the second embodiment of the invention. The image recording/reproducing operation according to the second embodiment is different from the image recording/reproducing operation according to the first embodiment shown in FIG. 3 in that the same image data on the first memory 223a and the second memory 223b is read out a plurality of times based on a speed setting input signal SS and the image is reproduced in a slow rewinding manner in the second mode and the third mode of the image recording/reproducing operation.

The speed setting input signal SS is inputted by a user through the switch 240 of the processor 200 for the electronic endoscope, and is data indicative of a degree of slow reproduction, such as double-slow (×2) or triple-slow (×3). The speed setting input signal SS is transmitted to the CPU 210 via the switch 240, and the CPU 210 controls the timing generator 225 based on the speed setting input signal SS.

As in the case of the first embodiment, in the first mode, when the CPU 210 detects pressing of the scope button 140 (T1), the CPU 210 controls the timing generator 225 to execute the first rewind reproduction process. When the first rewind reproduction process is executed, the timing generator 225 sets the first memory 223a to the writing-inhibited state (the readable state), switches the output of the switch circuit 223c to the first memory output MO1, and sets the first memory read address RA1 as the immediately previous value of the writing address WA, under control of the CPU 210. Then, when the double-slow (×2) is set to the speed setting input signal SS (the time period to T9, the time period from T10), the timing generator 225 decrements the first read address RA1 each time the input image data VIN corresponding to two frames is inputted to the frame memory 223. When the triple-slow (×3) is set to the speed setting input signal SS (the time period of T9 to T10), the timing generator 225 decrements the first read address RA1 each time the input image data VIN corresponding to three frames is inputted to the frame memory 223. In the case of FIG. 5, when the scope button 140 is pressed (T1), the immediately previous value of the writing address WA is "2", and data stored at this address is the input image data VIN of the "frame number: 242". In addition, when the scope button 140 is pressed (T1), the speed setting input signal SS is set to the double-slow (×2). Therefore, when the scope button 140 is pressed, initially the first memory read address RA1 is set to "2", the input image data VIN of the "frame number: 242" is read out. When the new input image data VIN is inputted to the frame memory 233, the first memory read address RA1 is kept at "2", and the input image data VIN of the "frame number 242" is read out again. Thus, during the time period to T9, the first memory read address RA1 is decremented each time the image data at the same address of the first memory 223a is read two times. When the speed setting input signal SS is set to the triple-slow (×3) at T9, thereafter (during the time period to T10) the first memory read address RA1 is decremented each time the image data at the same address of the first memory 223a is read out three times.

As described above, in this embodiment, when the first rewind reproduction process is executed, the image data stored in the first memory 223a is sequentially read out predetermined times from the latest data, and the slow rewind reproduction is performed. Therefore, according to the embodiment, the user is able to perform an operation (an operation to the freeze button 240a) for obtaining a still image while viewing a slow rewinding image. Therefore, it is possible to obtain a desired still image in a short time period. As in the case of the first embodiment, the slow rewinding reproduction is also performed when the mode moves from the first mode to the third mode. However, this operation is the same as the case when the mode moves from the first mode to the second mode, and therefore explanation thereof is omitted.

Third Embodiment

Next, an electronic endoscope apparatus 3 according to a third embodiment of the invention is explained with reference to FIG. 6. The electronic endoscope apparatus 3 according to the third embodiment of the invention has the same configuration as the electronic endoscope apparatus 1 according to the first embodiment shown in FIGS. 1 and 2, and is different from the first embodiment only in regard to the image recording/reproducing operation. In the following, the different point from the first embodiment is explained in detail.

Figure 6:
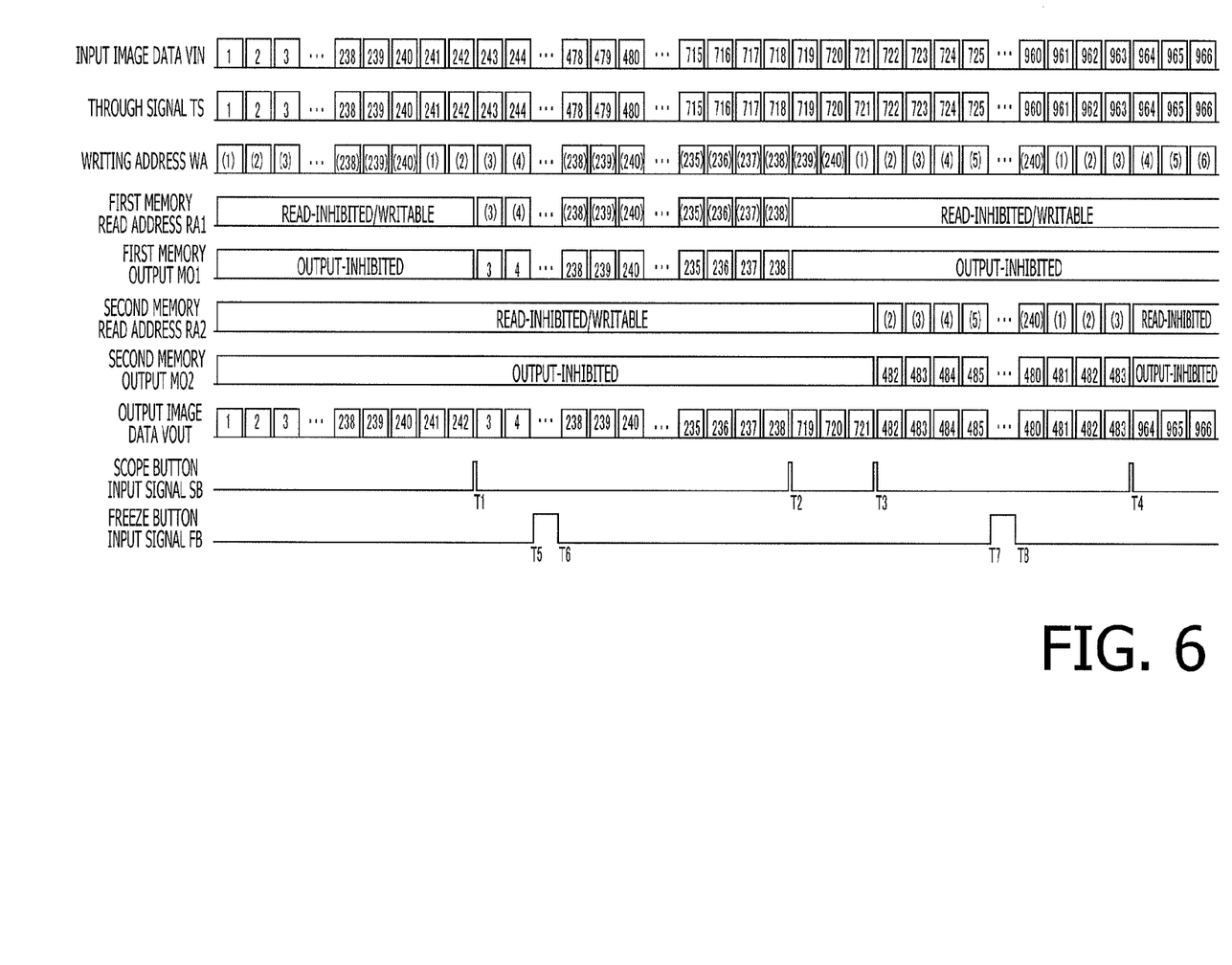
FIG. 6 is a timing chart illustrating an image record/reproduction operation executed in an electronic endoscope apparatus according to a third embodiment of the invention.

FIG. 6 is a timing chart illustrating the image recording/reproducing operation executed by the electronic endoscope apparatus 3 according to the third embodiment of the invention. The third embodiment is different from the image recording/reproduction operation of the electronic endoscope apparatus 1 according to the first embodiment shown in FIG. 3 in that the first rewind reproduction process and the second rewind reproduction process are not performed and the image data stored in the first memory 223a is read out in chronological order from the oldest data (i.e., a forward reproduction) in the second mode and the third mode of the image recording/reproduction operation.

When the CPU 210 detects pressing of the scope button 140 in the first mode (T1), the CPU 210 controls the timing generator 225 to execute a first forward reproduction process. When the forward reproduction process is executed, the timing generator 225 sets the first memory 223a to the writing-inhibited state (the readable state), switches the output of the switch circuit 223c to the first memory output MO1, and sets the first memory read address RA1 to the value obtained by adding "1" to the immediately previous value of the writing address WA. Then, the timing generator 225 decrements the first memory address RA1 each time the new input image data VIN is inputted to the frame memory 223. In the case of FIG. 6, when the scope button 140 is pressed (T1), the immediately previous value of the writing address WA is "2", and therefore the initial value of the first memory address RA1 is set to "3" which is obtained by adding "1" to "2". Then, the input image data VIN of the "frame number: 3" stored at this address is read out. Then, each time the new input image data VIN is inputted to the frame memory 223, the first memory read address RA1 is incremented as "4", "5", "6" . . . , the input image data VIN of "frame number: 4", "frame number: 5", "frame number: 6" . . . is read out sequentially.

As described above, when the first forward reproduction process according to the embodiment is executed, the image data stored in the first memory 223a is read out in chronological order from the oldest data, and therefore the video is reproduced and outputted in a forward direction. The first memory 223a according to the embodiment is constituted by a ring-type memory capable of storing 240 frames of image data. Therefore, after 240 frames of image data are reproduced, the video returns to the oldest frame again (frame number 3 in FIG. 3), and new frames are sequentially read out again.

As described above the image record/reproduction operation according to the third embodiment is different from the image record/reproduction operation of the first embodiment shown in FIG. 3 in that the image data stored in the first memory 223a is read out in chronological order from the oldest data. However, the third embodiment is the same as the first embodiment in that a still image is obtained in the second mode or the third mode, and provides advantages that a still image can be re-shot repeatedly without the need for waiting for storing of the image data in a memory. As in the case of the first embodiment, when the mode moves from the first mode to the third mode, a second forward reproduction process where the image data stored in the second memory 223b is read out in chronological order from the oldest data is performed. However, since this process is the same as the above described case where the mode moves from the first mode to the second mode, explanation thereof is omitted.

As described above, in the first, second and third embodiments of the invention, switching between the first to the third modes of the image record/reproduction operation is performed based on the operation of the scope button 140 of the electronic endoscope 100. However, the present invention is not limited to such a configuration. For example, switching between the first to the third modes may be performed based on the operation of the switch 240 of the processor 200 for the electronic endoscope. Similarly, the freeze button 240a and the speed setting button 240b are not limited to the switch 240 of the processor 200 for the electronic endoscope, and may be provided on the electronic endoscope 100.

What is claimed is:

1. A processor for an electronic endoscope for processing an image signal from the electronic endoscope and displaying an image on a monitor, comprising:
    an image data generator that generates a plurality of frames of image data from the image signal;
    first and second image storages, each of which stores the plurality of frames of image data;
    a signal processor that converts the plurality of frames of image data into a video signal which is displayed on the monitor; and
    a controller that controls the signal processor and the first and second image storages,
    wherein the controller performs control according to one of:
    a first mode, in which the plurality of frames of image data generated by the image data generator are sequentially converted into the video signal and are outputted, and are sequentially stored in the first and second image data storages;
    a second mode, in which the plurality of frames of image data stored in the first image storage are converted into the video signal and are outputted, and the plurality of frames of image data generated by the image data generator are sequentially stored in the second image storage; and
    a third mode, in which the plurality of frames of image data stored in the second image storage are converted into the video signal and are outputted, and the plurality of frames of image data generated by the image data generator are sequentially stored in the first image storage,
    wherein:
    in the second mode, a first reproduction mode and a second reproduction mode are switched from one to another, wherein, in the first reproduction mode, the plurality of frames of image data stored in the first image storage are successively converted into the video signal and are outputted, and, in the second reproduction mode, one of the plurality of frames of image data stored in the first image storage is repeatedly converted into the video signal and is outputted; and
    in the third mode, the first reproduction mode and the second reproduction mode are switched from one to another, wherein, in the first reproduction mode, plurality of frames of image data stored in the second mage storage are successively converted into the video signal and are outputted, and, in the second reproduction mode, one of the plurality of frames of image data stored in the second image storage is repeatedly converted into the video signal and is outputted;
    the processor for an electronic endoscope further comprising:
    a judger that receives an input of a control signal for switching from the first mode to the second or the third mode and for switching from the third mode or second mode to the first mode, and makes a judgment on which of the second mode and the third mode the controller switches to, when the control signal is inputted in the first mode,
    wherein the controller switches from the second mode to the first mode, when the control signal is inputted in the second mode,
    wherein, in response to the controller switching from the second mode to the first mode, the judger makes a judgment to switch from the first mode to the third mode only when the control signal is inputted within a predetermined time from a time when the controller switches from the second mode to the first mode, and makes a judgment to return from the first mode to the second mode when the control signal is inputted after the predetermined time has passed from the time when the controller switches from the second mode to the first mode,
    wherein the predetermined time is determined based on a maximum number of frames of image data which can be stored in the first image storage.

2. The processor for an electronic endoscope according to claim 1,
    wherein, when the controller switches from the first reproduction mode to the second reproduction mode in the second or third mode, a frame of the plurality of frames of image data outputted immediately before switching to the second reproduction mode is repeatedly converted into the video signal and is outputted.

3. The processor for an electronic endoscope according to claim 1,
    wherein, in the first reproduction mode of the second or third mode, the plurality of frames of image data stored in each of the first and second image storages are sequentially converted into the video signal in a reverse chronological order in regard to a stored time and are outputted.

4. The processor for an electronic endoscope according to claim 1,
wherein, in the first reproduction mode of the second or third mode, the plurality of frames of image data stored in each of the first and second image storages are sequentially converted into the video signal in a chronological order in regard to a stored time and are outputted.

5. The processor for an electronic endoscope according to claim 1,
wherein, in the first reproduction mode of the second or third mode, the plurality of frames of image data stored in each of the first and second image storages are successively converted into the video signal a plurality of times and are outputted.

6. The processor for an electronic endoscope according to claim 1,
wherein the judger makes a judgment such that the second mode and the third mode are alternately switched each time the control signal is inputted.

7. An electronic endoscope apparatus, comprising:
a processor for an electronic endoscope according to claim 4; and
an electronic endoscope connected to the processor for an electronic endoscope,
the electronic endoscope apparatus comprising:
a first inputter that receives an input for designating switching from the first mode to the second or third mode;
a second inputter that receives an input for switching from the first reproduction mode to the second reproduction mode in the second or third mode; and
a third inputter that receives an input for designating switching from the second and third modes to the first mode.

8. The electronic endoscope apparatus according to claim 7, wherein the first inputter is identical with the third inputter.

9. The electronic endoscope apparatus according to claim 7, further comprising a fourth inputter that receives an input for switching from the second reproduction mode to the first reproduction mode in the second mode or the third mode.

10. The electronic endoscope apparatus according to claim 9, wherein the second inputter is identical with the fourth inputter.

* * * * *